United States Patent
McCormick et al.

(10) Patent No.: US 9,750,912 B2
(45) Date of Patent: Sep. 5, 2017

(54) INTUBATION DEVICE

(75) Inventors: Laura McCormick, Ann Arbor, MI (US); Douglas Mullen, Cambridge, MA (US); Sabina Siddiqui, Ann Arbor, MI (US); Michael Deininger, Pinckney, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 572 days.

(21) Appl. No.: 14/115,196

(22) PCT Filed: May 3, 2012

(86) PCT No.: PCT/US2012/036290
§ 371 (c)(1),
(2), (4) Date: Jan. 16, 2014

(87) PCT Pub. No.: WO2012/151381
PCT Pub. Date: Nov. 8, 2012

(65) Prior Publication Data
US 2014/0123976 A1    May 8, 2014

Related U.S. Application Data (60) Provisional application No. 61/482,267, filed on May 4, 2011.

(51) Int. Cl.
*A61M 16/00* (2006.01)
*A61M 16/04* (2006.01)

(52) U.S. Cl.
CPC .............................. *A61M 16/0488* (2013.01)

(58) Field of Classification Search
CPC .. A61M 16/0488; A61M 25/09; A61M 25/01; A61M 25/0102; A61M 25/0105; A61M 25/0133
See application file for complete search history.

(56) References Cited

U.S. PATENT DOCUMENTS 2,498,692 A * 2/1950 Mains .................... A61M 25/10
                                                              604/915
3,060,972 A * 10/1962 Sheldon ............... A61B 1/0055
                                                              138/120

(Continued)

FOREIGN PATENT DOCUMENTS

| JP | 08-047536 A | 2/1996 |
| WO | WO-2007138569 A2 | 12/2007 |
| WO | WO-2010065566 A2 | 6/2010 |

OTHER PUBLICATIONS

Supplementary European Search Report in Corresponding European Patent Application No. EP 12 779 414.7, dated Oct. 31, 2014.

(Continued)

*Primary Examiner* — Bradley Philips
*Assistant Examiner* — Victoria Leszczak
(74) *Attorney, Agent, or Firm* — Harness, Dickey & Pierce, P.L.C.

(57) ABSTRACT

An intubation device having a main body portion defining a first longitudinal axis, a distal tip portion coupled to the main body portion and defining a second longitudinal axis, and a deflection system having a single drive member extending within at least the distal tip portion and coupled thereto. The deflection system is operable to exert a tensile force upon the distal tip portion to articulate the distal tip portion relative to the main body portion between a resting position and a positive incline position and a negative incline position.

18 Claims, 6 Drawing Sheets

(56) References Cited

U.S. PATENT DOCUMENTS

| | | | |
|---|---|---|---|
| 3,314,431 A * | 4/1967 | Smith, Jr. | A61M 16/0488 128/200.26 |
| 3,557,780 A * | 1/1971 | Sato | A61B 1/0055 356/241.4 |
| 3,572,325 A * | 3/1971 | Bazell | A61B 1/0055 138/120 |
| 3,669,098 A * | 6/1972 | Takahashi | A61B 1/0055 600/114 |
| 3,802,440 A * | 4/1974 | Salem | A61M 16/0488 128/200.26 |
| 4,840,172 A * | 6/1989 | Augustine | A61M 16/0488 128/207.14 |
| 5,095,888 A | 3/1992 | Hawley | |
| 5,259,377 A | 11/1993 | Schroeder | |
| 5,306,245 A | 4/1994 | Heaven | |
| 5,318,008 A * | 6/1994 | Bullard | A61B 1/0056 600/139 |
| 5,392,791 A * | 2/1995 | Nyman | A61N 1/056 600/585 |
| 5,441,483 A | 8/1995 | Avitall | |
| 5,445,161 A | 8/1995 | Huang | |
| 5,607,386 A | 3/1997 | Flam | |
| 5,791,338 A * | 8/1998 | Merchant | A61M 16/0488 128/200.26 |
| 5,842,194 A | 11/1998 | Arbuckle | |
| 5,842,973 A | 12/1998 | Bullard | |
| 5,885,248 A | 3/1999 | Denton | |
| 6,164,277 A | 12/2000 | Merideth | |
| 6,251,069 B1 | 6/2001 | Mentzelopoulos et al. | |
| 6,266,442 B1 | 7/2001 | Laumeyer et al. | |
| 6,321,749 B1 | 11/2001 | Toti et al. | |
| 6,501,857 B1 | 12/2002 | Gotsman et al. | |
| 6,587,601 B1 | 7/2003 | Hsu et al. | |
| 6,647,139 B1 | 11/2003 | Kunii et al. | |
| 6,678,545 B2 | 1/2004 | Bucholz | |
| 6,728,635 B2 | 4/2004 | Hamada et al. | |
| 6,746,422 B1 | 6/2004 | Noriega et al. | |
| 6,757,557 B1 | 6/2004 | Bladen et al. | |
| 6,776,765 B2 * | 8/2004 | Soukup | A61B 5/0086 600/435 |
| 6,875,169 B2 | 4/2005 | Berci et al. | |
| 7,031,496 B2 | 4/2006 | Shimano et al. | |
| 7,044,909 B2 | 5/2006 | Berci et al. | |
| 7,072,704 B2 | 7/2006 | Bucholz | |
| 7,089,928 B2 | 8/2006 | Besharim et al. | |
| 7,137,981 B2 | 11/2006 | Long | |
| 7,174,202 B2 | 2/2007 | Bladen et al. | |
| 7,221,797 B2 | 5/2007 | Koshizen et al. | |
| D580,549 S | 11/2008 | Schwartz et al. | |
| D603,958 S | 11/2009 | Schwartz et al. | |
| D605,758 S | 12/2009 | Schwartz et al. | |
| 7,658,708 B2 | 2/2010 | Schwartz et al. | |
| 7,747,319 B2 | 6/2010 | Freeman | |
| 7,774,054 B2 | 8/2010 | Myklebust | |
| 7,892,186 B2 * | 2/2011 | Soukup | A61M 25/0136 600/585 |
| 7,925,339 B2 | 4/2011 | Wik | |
| 8,095,336 B2 | 1/2012 | Goncalves et al. | |
| 8,684,953 B2 * | 4/2014 | Cabiri | A61M 25/0138 600/585 |
| 8,746,239 B2 * | 6/2014 | Yoshida | A61M 16/0488 128/200.26 |
| 9,138,566 B2 * | 9/2015 | Cabiri | A61B 17/00234 |
| 2005/0075661 A1 | 4/2005 | Levine et al. | |
| 2009/0044799 A1 | 2/2009 | Qiu | |
| 2009/0125001 A1 | 5/2009 | Anderson et al. | |
| 2010/0108060 A1 | 5/2010 | Pecherer et al. | |
| 2010/0224187 A1 | 9/2010 | Dalton | |
| 2011/0137127 A1 | 6/2011 | Schwartz et al. | |
| 2011/0144514 A1 | 6/2011 | Booker | |
| 2011/0178419 A1 | 7/2011 | Wood et al. | |
| 2011/0196204 A1 * | 8/2011 | Setty | A61B 1/00052 600/120 |
| 2011/0201882 A1 | 8/2011 | Schwartz et al. | |
| 2011/0263935 A1 | 10/2011 | Qiu | |
| 2011/0265795 A1 | 11/2011 | Tagawa et al. | |
| 2013/0255671 A1 * | 10/2013 | Furman | A61M 16/0488 128/200.26 |
| 2015/0246201 A1 * | 9/2015 | Kirn | A61M 16/0488 128/202.27 |

OTHER PUBLICATIONS

International Search Report and Written Opinion (both in English) for PCT/US2012/036290, mailed Nov. 28, 2012; ISA/KR.

\* cited by examiner

INTUBATION DEVICE

CROSS-REFERENCE TO RELATED APPLICATIONS

This application claims the benefit of U.S. Provisional Application No. 61/482,267, filed on May 4, 2011. The entire disclosure of the above application is incorporated herein by reference.

GOVERNMENT INTEREST

This invention was made with government support under FD-R-003787 awarded by the Food and Drug Administration. The government has certain rights in the invention.

FIELD

The present disclosure relates to an intubation device and, more particularly, relates to an intubation device having a novel flexural capability.

BACKGROUND AND SUMMARY

This section provides background information related to the present disclosure which is not necessarily prior art. This section also provides a general summary of the disclosure, and is not a comprehensive disclosure of its full scope or all of its features.

Over twenty million intubations occur in the United States each year. Endotracheal intubation is a procedure where a tube is placed through the mouth and into the trachea to create an artificial circuit for breathing. In the emergency setting, this life-saving procedure is most often performed by health care personnel with the least amount of experience and in the most difficult of circumstances. Failure rates in emergency intubations when conducted by emergency medical personnel range from 10-50%, incurring high human and healthcare costs, not limited to brain damage and death. There are 180,000 deaths per year in the pre-hospital emergency setting alone from misplaced endotracheal tubes and many more when including misplaced tubes in the hospital setting. The cost of failed or difficult intubation can be very high as reflected in a private settlement in excess of $15 million in 2002.

Over half of emergency intubations are performed by first-responders in the pre-hospital setting. The majority of first-responders are in their middle twenties, have minimal training and an average of only three years of experience. First responders are mandated to perform only five intubations to be certified, yet studies have shown that 15 to 20 intubations are necessary to attain basic skill proficiency. Once in the field, 67% of paramedics will only perform one or two intubations per year. The training standard for paramedics is also significantly less than the minimum requirement of 200 intubations for emergency medicine clinicians or over 400 for anesthesiologists.

The intubation device of the present teachings enables less experienced practitioners to be as successful as highly trained anesthesiologists because the device enables enhanced control of the distal tip of the intubation device for placing the tube within the trachea of the patient.

The intubation device of the present teachings is a medical device that is designed to improve the efficacy and safety of emergency intubations, especially in the hands of less-skilled practitioners. The intubation device can comprise a main body portion defining a first longitudinal axis, a distal tip portion coupled to the main body portion and defining a second longitudinal axis, and a deflection system having a single drive member extending within at least the distal tip portion and coupled thereto. The deflection system is operable to exert a tensile force upon the distal tip portion to articulate the distal tip portion relative to the main body portion between a resting position and a positive incline position and a negative incline position. In some embodiments, the intubation device can comprise a plurality of notches formed along the distal tip portion and can be actuated in response to movement of a slider member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, an intubation device is provided having advantageous construction and method of use. More particularly, the intubation device of the present teachings provides enhanced flexural movement of the distal tip portion thereof and is capable of both positive and negative flexural movement (relative to a longitudinal reference axis of the main body) generally about a single axis transverse to the longitudinal axis of the main body. This flexural movement can be controlled using a user-actuated input that is conveniently and efficiently coupled with a deflection mechanism for actuating the distal tip portion. In some embodiments, this deflection mechanism can comprise a single drive cable for the positive and negative flexural movement. The intubation device is sized to be slid within an endotracheal tube during intubation. Those skilled in the art will recognize additional advantages of the intubation device of the present teachings in light of the discussion herein.

Figure 1:
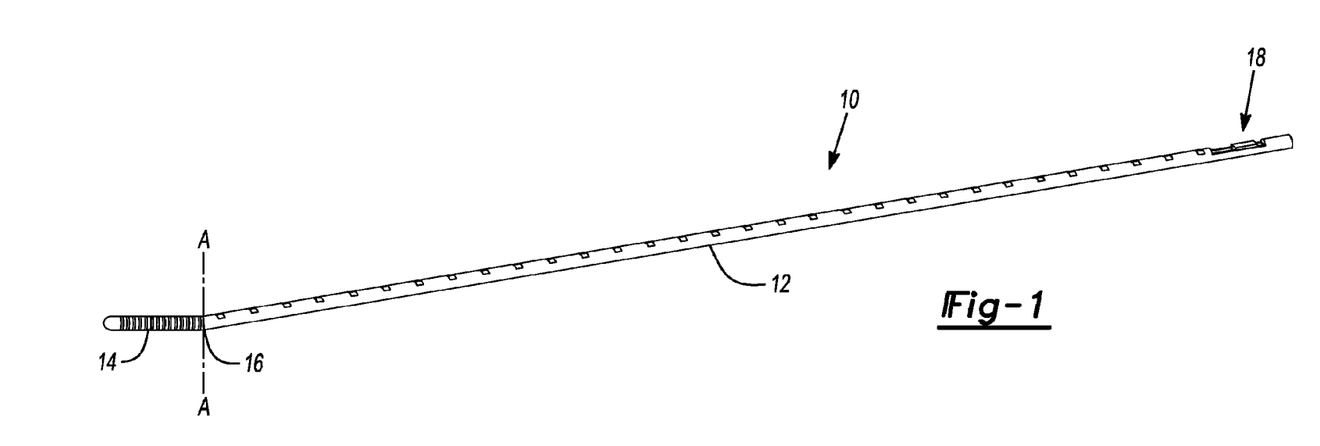
FIG. 1 is a perspective view illustrating an intubation device according to the principles of the present teachings.
Figure 2:
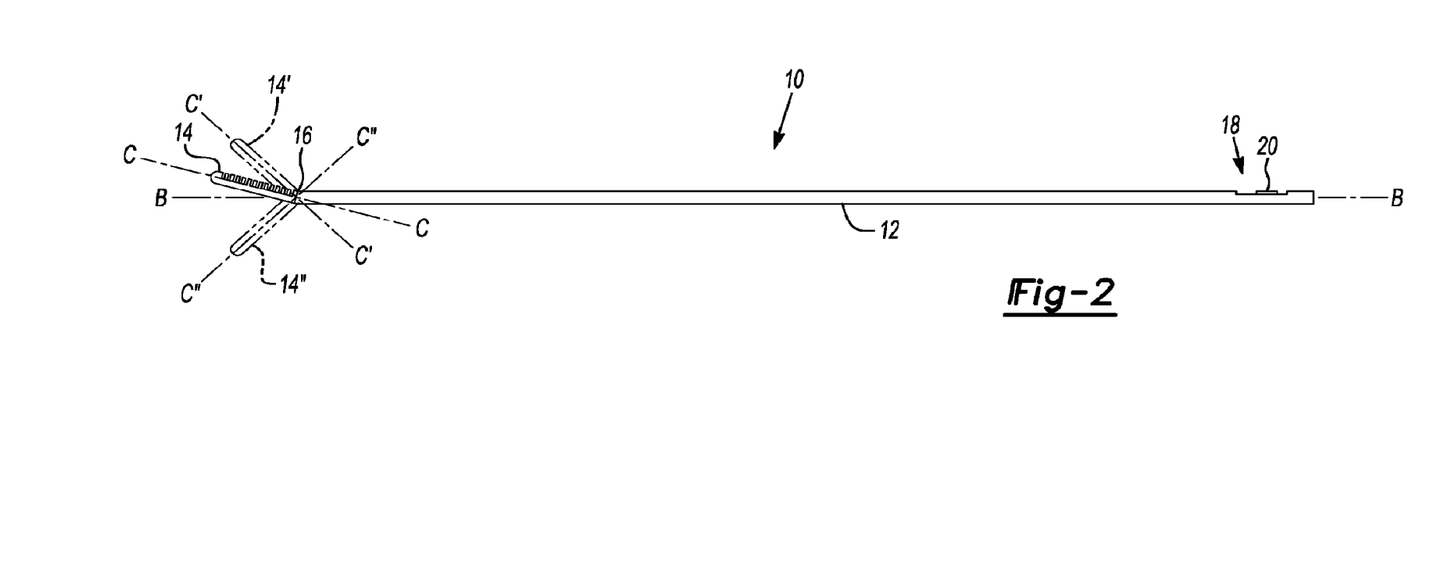
FIG. 2 is a side view illustrating the intubation device of FIG. 1.

With reference to the several figures, an intubation device 10 according to the principles of the present teachings is illustrated. In some embodiments, as illustrated in FIGS. 1 and 2, intubation device 10 can comprise a generally elongated main body portion 12 terminating at a distal tip portion 14. Main body portion 12 and distal tip portion 14 can be joined along an interface 16 that, in some embodiments, is a solidly and/or integrally formed interconnection. That is, in some embodiments, main body portion 12 and distal tip portion 14 can be simultaneously formed to define a single continuous member. However, in some embodiments, it may be desirable to form main body portion 12 and distal tip portion 14 as separate members that can be subsequently joined through known processes (e.g. ultrasonic welding, bonding, etc.). It should be understood that in some embodiments, interface 16 of intubation device 10 may be a rigid connection and/or region that generally inhibit deflection, thus encouraging deflection in distal tip portion 14 due to its unique construction as will be described herein.

Main body portion 12 and distal tip portion 14 can define a generally constant cross-sectional shape and size. However, it should be appreciated that alternative cross-sectional shapes and/or varying cross-sectional dimensions are anticipated by the present disclosure. Such variations in cross-sectional shape and/or size can enhance articulation in some embodiments.

With continued reference to FIGS. 1 and 2, intubation device 10 can comprise a deflection mechanism 18 that is operable to urge controlled deflection of distal tip portion 14 in response to input from the user. That is, according to the present teachings, actuation of deflection mechanism 18 by a user can result in controlled deflection of distal tip portion 14 generally about an axis A-A (FIGS. 1 and 3-5). In some embodiments, distal tip portion 14 can articulate or flex from a rest position (see FIGS. 1-5) to a positive incline position (FIG. 2) and a negative incline position (FIG. 2). More particularly, deflection mechanism 18 can be used to urge distal tip portion 14 to articulate or flex from the rest position. In some embodiments, this rest position defines a predetermined initial inclination of distal tip portion 14, generally referenced as longitudinal axis C-C of distal tip portion 14 relative to a longitudinal axis B-B of main body portion 12. In some embodiments, this rest position of distal tip portion 14 can define an initial angle between longitudinal axis CC of distal tip portion 14 and longitudinal axis B-B of main body portion 12 of about 10 degrees to about 20 degrees and, more particularly, about 15 degrees. However, it should be appreciated that this initial angle can be different than 15 degrees, depending on particular applications or anatomical considerations. Articulation or flexing of distal tip portion 14 by deflection mechanism 18 can result in increased inclination of distal tip portion 14 to a positive incline position, generally referenced as distal tip portion 14' in FIG. 2. In this positive incline position, distal tip portion 14' is inclined at a greater angle than the initial inclination angle of the rest position. As such, distal tip portion 14' generally defines a longitudinal axis C'-C' that, in some embodiments, can be about 35 to about 40 degrees relative to longitudinal axis B-B of main body portion 12. Articulation or flexing of distal tip portion 14 by deflection mechanism 18 can also result in decreased inclination of distal tip portion 14 to a negative incline position, generally referenced as distal tip portion 14" in FIG. 2. In this negative incline position, distal tip portion 14" is declined at an angle less than the initial inclination angle of the rest position. As such, distal tip portion 14" generally defines a longitudinal axis C"-C" that, in some embodiments, can be about 10 to about 15 degrees below the longitudinal axis B-B of main body portion 12. As such, distal tip portion 14 can be articulated or flexed to any position between negative incline position (e.g. about −10 to about −20 degrees below horizontal axis B-B or, more particularly, about −10 to about −15 degrees) and positive incline position (e.g. about 30 to about 40 degrees above horizontal axis B-B or, more particularly about 35 degrees to about 40 degrees). In this way, distal tip portion 14 can be manipulated conveniently and simply to follow the anatomical pathways of nearly any patient. It should be recognized however, that the aforementioned angles and rest positions can be varied. Thus, in some embodiments, greater or lesser inclination ranges can be used and/or the inclination angle of the rest position can be decreased, increased, and/or eliminated.

Figure 8:
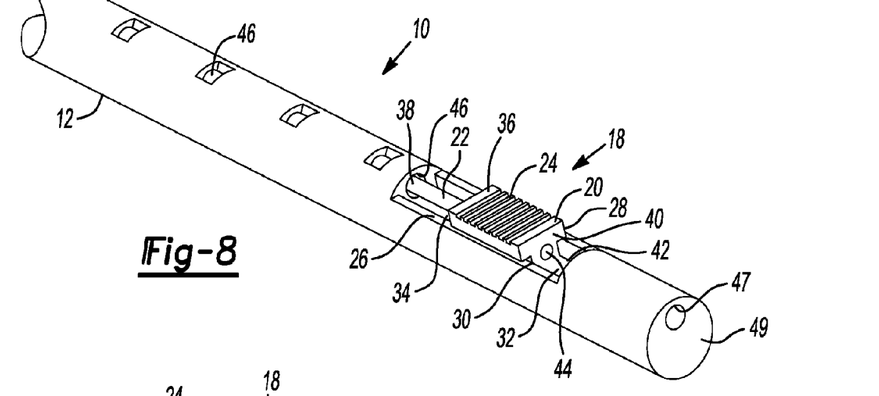
FIG. 8 is an enlarged perspective view of the main body portion and slider member of the intubation device of FIG. 1.

With reference to FIGS. 1, 2, 8, and 9, in some embodiments, deflection mechanism 18 can comprise an actuation member 20 and a drive member 22 coupled with at least a portion of distal tip portion 14. More particularly, as illustrated in FIG. 8, actuation member 20 can comprise a slider member 24 slidably disposed and captured within a slider channel 26 formed in main body portion 12. Slider member 24 can comprise a generally-textured (e.g. serrated) exterior surface portion 28 having a series of ridges to enhance contact with a user's thumb or fingers. Slider member 24 can comprise a central region 30 having a reduced cross-sectional width terminating at an enlarged lower region 32. Enlarged lower region 32 can be sized and shaped to be slidably received within a corresponding channel 34 formed in main body portion 12 to permit fore and aft sliding translation of slider member 24. The range of such sliding translation can be limited through the use of physical stops preventing further translation of slider member 24 relative to main body portion 12. In some embodiments, a fore end 36 of slider member 24 can contact a fore edge 38 of slider channel 26 to prevent further sliding movement of slider member 24. In this regard, contact of fore end 36 of slider member 24 against fore edge 38 of slider channel 26 can prevent further articulation of distal tip portion 14 into the negative incline position. Similarly, in some embodiments, an aft end 40 of slider member 24 can contact an aft edge 42 of slider channel 26 to prevent further sliding movement of slider member. In this regard, contact of aft end 40 of slider member 24 against aft edge 42 of slider channel 26 can prevent further articulation of distal tip portion 14 into the positive incline position. Release of application force on deflection mechanism 18 results in the return of distal tip portion 14 back to its rest position, in response to the elastic qualities of the materials chosen for distal tip portion 14.

Figure 9:
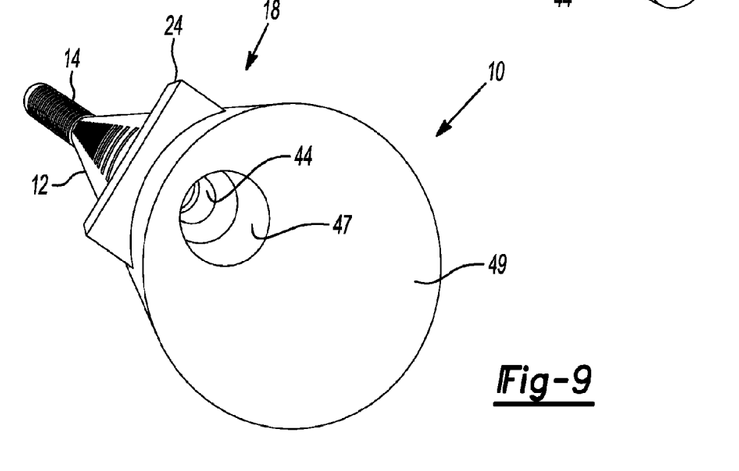
FIG. 9 is an end view of the main body portion and slider member of the intubation device of FIG. 1.

In some embodiments, as illustrated in FIG. 9, an exterior shape of slider member 24, namely exterior surface portion 28, can be selected to permit intubation device 10 and, particularly, slider member 24 to be slidably disposed within a conventional tracheal tube.

With reference to FIGS. 8 and 9, drive member 22 can be a generally flexible member that is capable of operating in response to both tensile and compressive forces.

Figure 4:
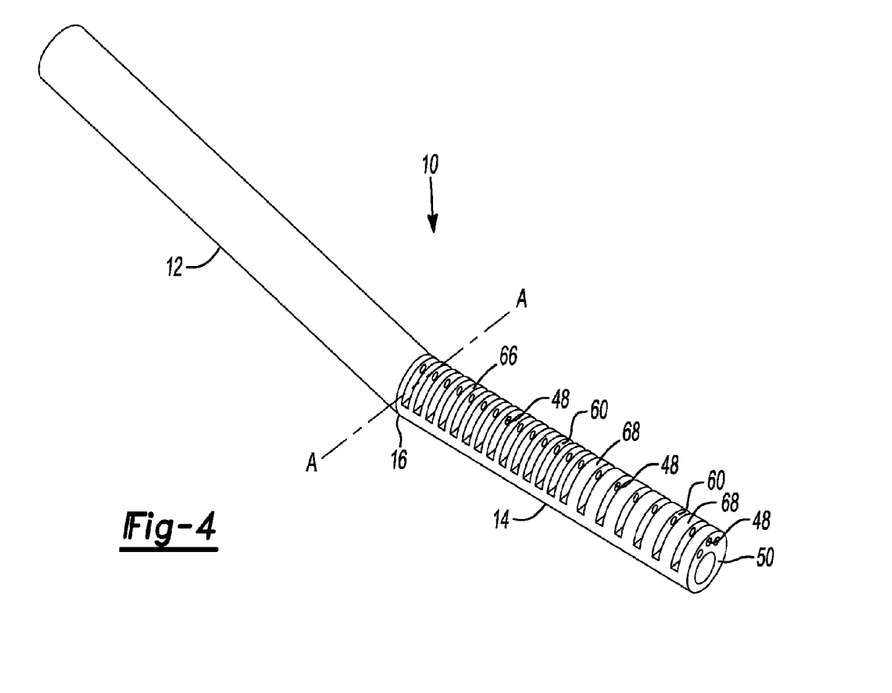
FIG. 4 is a top perspective view of the distal tip portion of the intubation device of FIG. 1.
Figure 5:
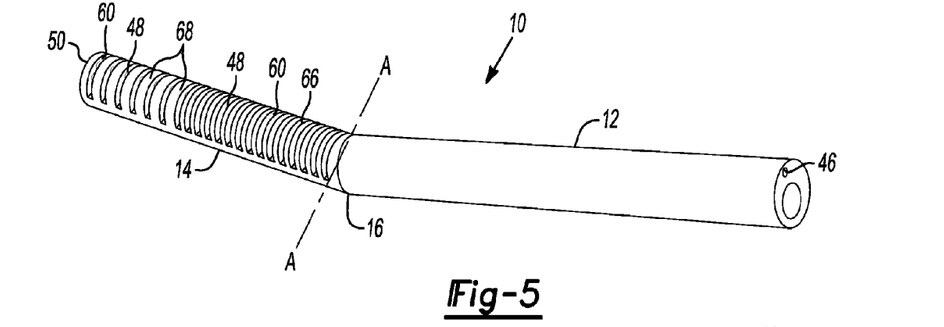
FIG. 5 is another top perspective view of the distal tip portion of the intubation device of FIG. 1.
Figure 6:
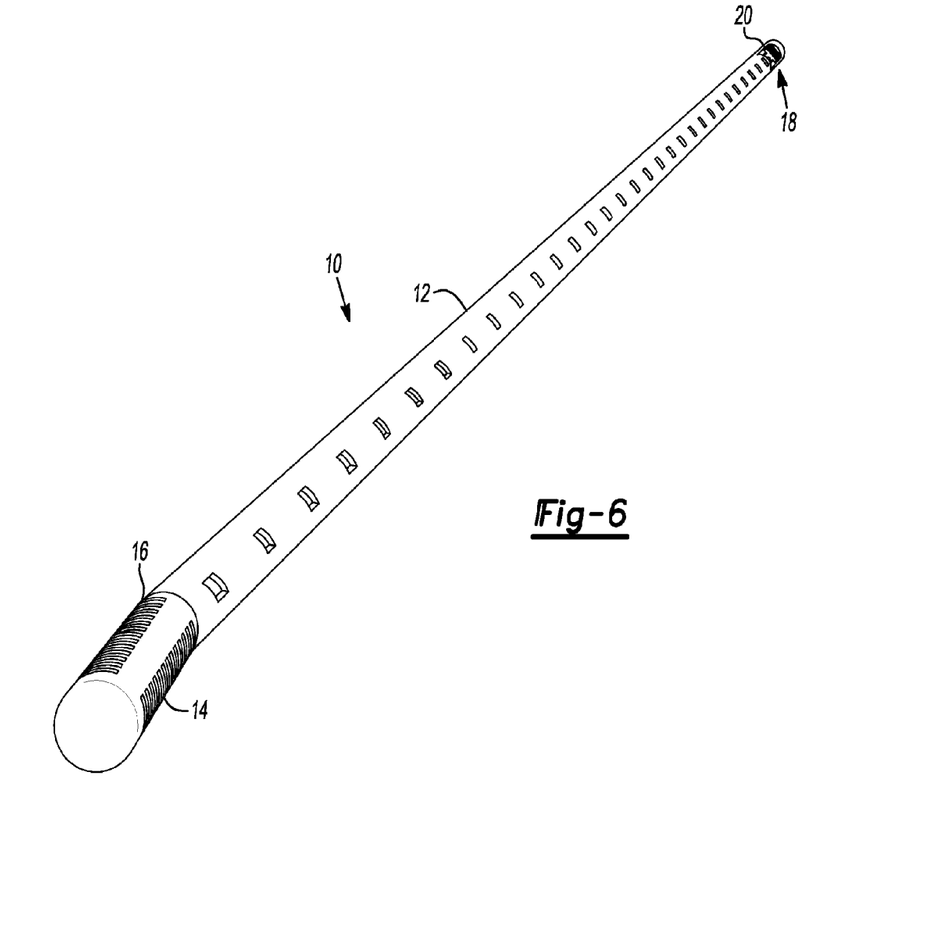
FIG. 6 is an end perspective view of the intubation device of FIG. 1.
Figure 7:
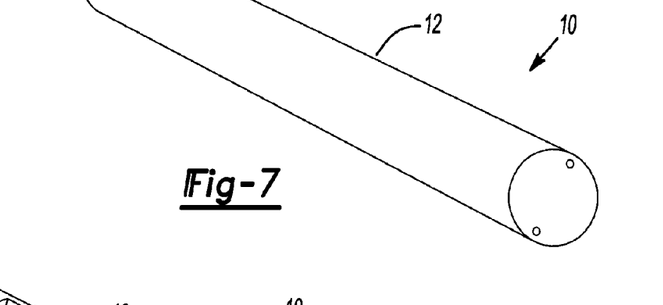
FIG. 7 is a partial view of the intubation device of FIG. 1.
Figure 10:
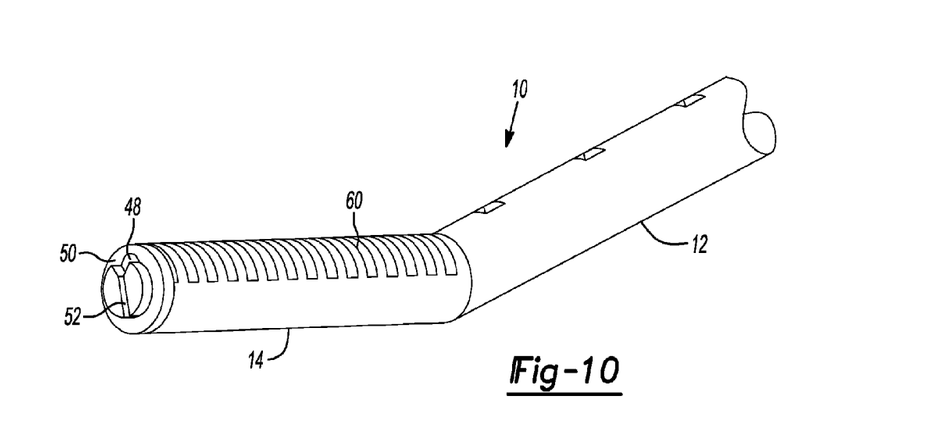
FIG. 10 is an end view of the distal tip portion and the bifurcated end of the intubation device of FIG. 1.
Figure 11:
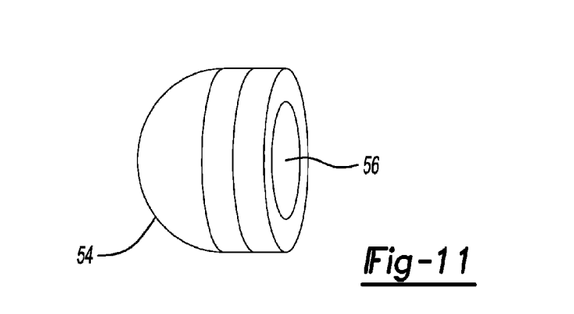
FIG. 11 is a perspective view of the cap member of the intubation device of FIG. 1.

A first end (proximal) of drive member 22 can be fixedly coupled to slider member 24 for movement therewith and an opposing end (distal) can be fixedly coupled to at least a portion of distal tip portion 14. More particularly, in some embodiments, drive member 22 can be fixedly coupled within an aperture 44 formed in at least one of central region 20 and/or exterior surface portion 28 of slider member 24 using a press fit connection, interference fit connection, fastener, bonding agent (e.g. epoxy) or other conventional retaining system. Drive member 22 can then extend through one or a plurality of apertures 46 formed through main body portion 12 (FIG. 8) and additionally through a plurality of apertures 48 formed in distal tip portion 14 (FIGS. 4 and 5). In some embodiments, as illustrated in FIGS. 8 and 9, an aperture 47 can be disposed in proximal end 49 of main body portion 12 to facilitate insertion of drive member 22 into main body portion 12 and distal tip portion 14. Drive member 22 can then be fixedly retained at a distal end 50 of distal tip portion 14. As illustrated in FIGS. 10 and 11, drive member 22 can extend from a final aperture 48 in distal tip portion 14 and then be retained within a transverse slot or bifurcated end 52 formed in distal end 50 of distal tip portion 14. Drive member 22 can be fixedly coupled therein using a press fit connection, interference fit connection, fastener, bonding agent (e.g. epoxy) or other conventional retaining system. A cap member 54 (FIGS. 6 and 11) can be fixedly coupled over distal end 50 such that an interior volume 56 receives the enlarged bifurcated end of distal end 50 using any one of a number of fastening techniques, such as a press fit connection, interference fit connection, threadedly engaging, bonding agent (e.g. epoxy) or other conventional retaining system. Cap member 54 can be made of a material having a Shore durometer of about 40 to about 50.

In some embodiments, the one or a plurality of apertures 46 in main body portion 12 and/or the plurality of apertures 48 in distal tip portion 14 can be offset above axis B-B of main body portion 12 and axis C-C of distal tip portion 14, respectively, to provide enhance mechanical advantage in exerting the tensile or compressive forces upon distal tip portion 14. By way of non-limiting example, in some embodiments apertures 46 and 48 can be about 1.5 mm in diameter and located about 1.35 mm above axis B-B.

In some embodiments, drive member 22 is a wire or spring steel member that is capable of exerting both tensile force to articulate or flex distal tip portion 14 into the positive incline position and a compressive force to articulate or flex distal tip portion 14 into the negative incline position. Although it should be appreciated that the shape, contour, materials selected, and overall design of distal tip portion 14 will affect the design of the drive member 22, it has been found that the following wire can be used. Specifically, drive member 22 can be a 1080 carbon steel, spring temper wire having a diameter of about 0.015" (commonly called "music wire"). Alternative materials can also be used, including 1) spring temper stainless steel wires including type 304, 316, PTFE-coated type 304, 2) spring temper carbon steels including 1065, 1075 (and 1080, as indicated above), 3) alloy 510 phosphor bronze, and 4) shape-memory alloy such as Nitinol (Nickel titanium).

In operation, aft movement of slider member 24 (e.g. in a direction such that aft end 40 of slider 24 approaches and possibly contacts aft edge 42 of slider channel 26) causes slider member 24 to apply a tensile force to drive member 22 thereby articulating distal tip portion 14 into the positive incline position. Similarly, fore movement of slider member 24 (e.g. in a direction such that fore end 36 of slider member 24 approaches and possibly contacts fore edge 38 of slider channel 26) cause slider member 24 to apply a compressive force to drive member 22 thereby articulating distal tip portion 14 into the negative incline position. As described herein, it should be understood that through actuation of slider member 24 between the fore edge 38 and aft edge 42 of slider channel 26, distal tip portion 14 can be positioned at any location or at any inclination between the positive incline position and the negative incline position.

With particular reference to FIGS. 3-6, in some embodiments, distal tip portion 14 can comprise one or more notches 60 formed along at least one side of distal tip portion 14. In some embodiments, this at least one side can be generally disposed along a side that is in line with the direction of articulation so at to encourage flexural movement of distal tip portion 14. That is, notches 60 can be formed along an appropriate side of distal tip portion 14 to remove binding material therefrom to permit articulation. As such, it should be understood that in some embodiments, notches 60 can be disposed along an underside of distal tip portion (when viewed in FIGS. 2 and 3); although improved performance can be gained disposing notches 60 along a top side of distal tip portion.

Figure 3:
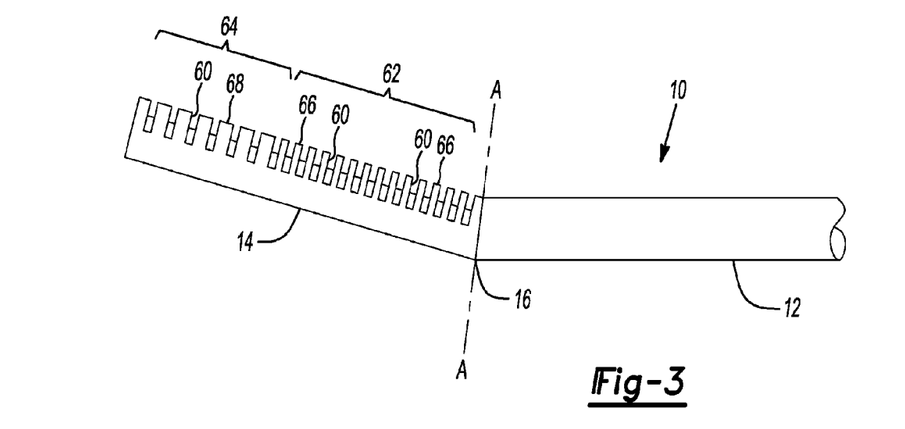
FIG. 3 is an enlarged side view illustrating the distal tip portion of the intubation device of FIG. 1.
Figure 12:
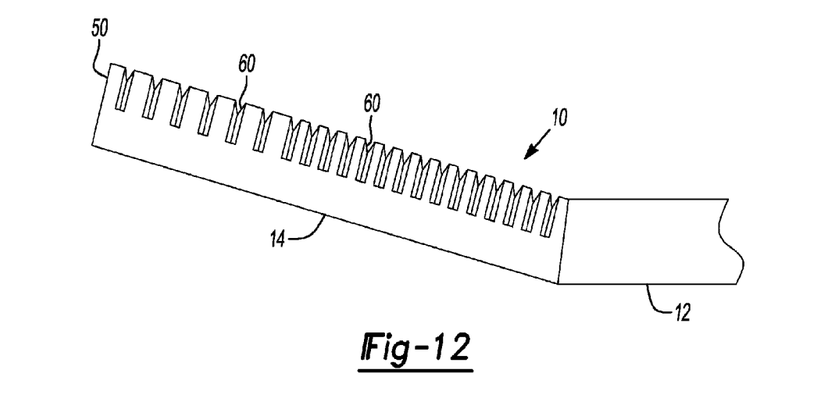
FIG. 12 is an enlarged side view illustrating an alternative notch configuration according to the principles of the present teachings.

In some embodiments, notches 60 can be sized, spaced, and/or otherwise shaped to encourage a particular or beneficial flexural behavior. As illustrated in FIG. 3, in some embodiments, notches 60 can comprise at least a first section 62 of notches 60 and a second section 64 of notches 60. First section 62 can define a plurality of generally narrowly sized ribs 66 and generally narrow and equally spaced notches 60. Each of the notches 60 of first section 62 can further define a generally rectangular cutout shape. It has been found that this rectangular cutout shape provides enhance flexural behavior; although alternative cutout shaped can be used, such as triangular (see FIG. 12), circular, arcuate, and the like. In some embodiments, the width of notches 60 and the interspersed ribs 66 can be generally equal in first section 62. Similarly, second section 64 can define a plurality of generally wider sized ribs 68 and generally narrow and equally spaced notches 60. Each of the notches 60 of second section 64 can further define a generally rectangular cutout shape. In some embodiments, the width of interspersed ribs 66 of second section 64 can be generally twice the width of notches 60 within second section 64. However, again, the specific size, shape, and arrangement of notches 60 and ribs 66 can be varied depending on the specific application. By way of non-limiting example, in some embodiments, notches 60 can have a width of about 1 mm and a depth of about 2.5 mm.

In some embodiments, intubation device 10 can be made of a flexible polymeric or metallic material. More particularly, intubation device 10 and, in particular, distal tip portion 14 can be made of a material having a Shore durometer of about 86 and, in some embodiments, distal tip portion 14 can have different materials used between ribs (e.g. within notches 60) having a Shore durometer of about 40. In some embodiments, materials can be chosen for distal tip portion 14 having a different and perhaps more flexible elastic modulus than main body portion 12. Moreover, in some embodiments, distal tip portion 14 can have a different material having a more flexible elastic modulus (or a less flexible elastic modulus, if desired) used between ribs (e.g. within notches 60) as opposed to adjacent areas (e.g. ribs). The outer diameter of intubation device 10 can be in the range of about 1 mm to about 12 mm, or more particularly about 5 mm. The length of intubation device 10 can be in the range of about 20 cm to 60 cm, with distal tip portion 14 being about 1 mm to about 60 mm, or more particularly about 34.5 mm. In some embodiments, distal tip portion 14 can be made of a material different than main body portion 12. In some embodiments, distal tip portion 14 can be made of a flexible polymer or a jointed rigid material.

Figure 13:
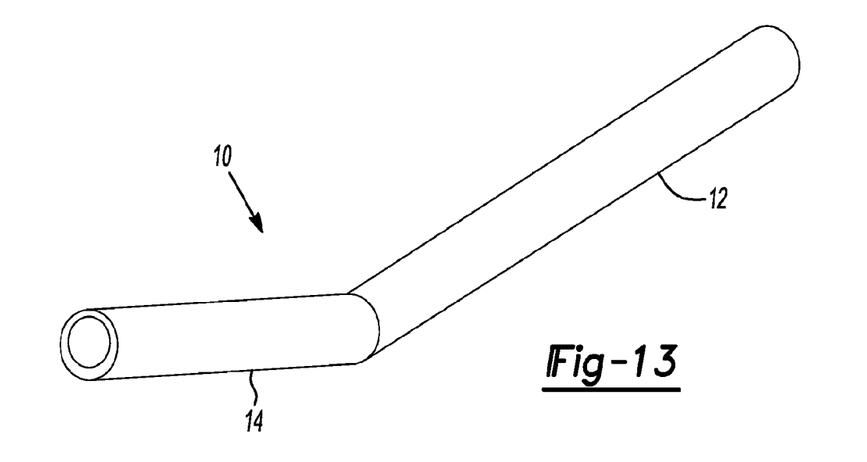
FIG. 13 is an enlarged end view illustrating an alternative deflection system according to the principles of the present teachings.
Figure 14:
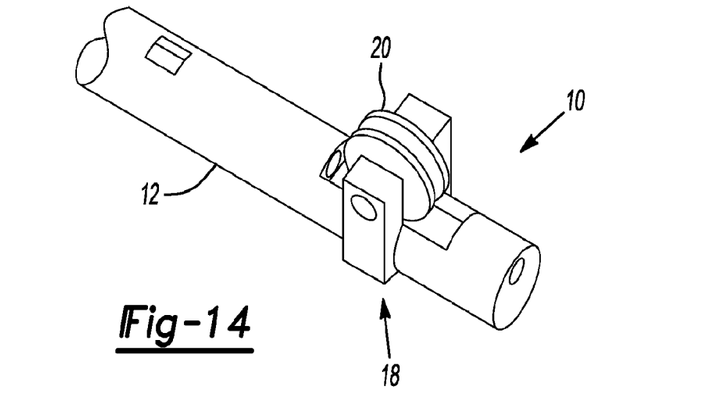
FIG. 14 is an enlarged perspective view of the main body portion and an alternative actuation member according to the principles of the present teachings.
Figure 15:
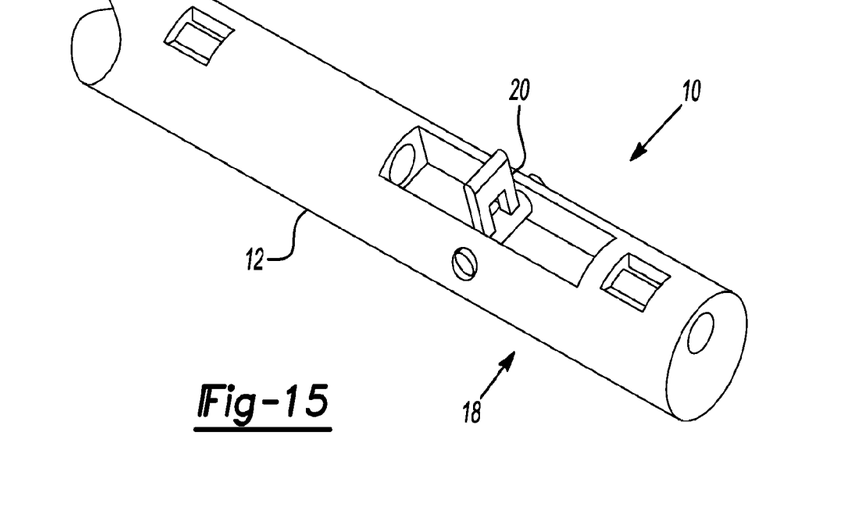
FIG. 15 is an enlarged perspective view of the main body portion and an alternative actuation member according to the principles of the present teachings.

It should be appreciated that alternatives to the present embodiments are possible. For example, in some embodiments, as mentioned herein, the shape of notches 60 can be varied to achieve different flexural control and behavior (see FIG. 12). Moreover, the shape, size, distribution, material, material hardness, and other parameters of notches, ribs, and distal tip portion can be varied at various positions along intubation device 10 to achieve different flexural control and behavior. Still further, in some embodiments, deflection mechanism 18 can employ suction or pressurized fluid (e.g. liquid or gas) contained within a generally sealed chamber within intubation device 10 to cause a flexing response (see FIG. 13). Additionally, in some embodiments, slider member 24 can be replaced with a roller member or rocker member (see FIGS. 14 and 15) that can be used to actuate drive member 22.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An endotracheal intubation device comprising:
a generally elongated main body portion defining a first longitudinal axis (B-B);
a distal tip portion coupled to said main body portion at an interface, said distal tip portion defining a second longitudinal axis (C-C), said interface comprising a generally rigid connection to establish said distal tip portion in a rest position defined by a predetermined initial inclination of said second longitudinal axis (C-C) relative to said first longitudinal axis (B-B), said predetermined initial inclination being in the range of about 10 degrees to about 20 degrees measured from said first longitudinal axis (B-B); and
a deflection system extending within at least said distal tip portion and coupled thereto, said deflection system operable to exert a force upon said distal tip portion to articulate said distal tip portion relative to said main body portion between said resting position and a positive incline position, said positive incline position defining a first angle between said first longitudinal axis (B-B) and a positive inclined longitudinal axis (C'-C'), said first angle being greater than said predetermined initial inclination, said deflection system further operable to exert a force upon said distal tip portion to articulate said distal tip portion relative to said main body portion between said resting position to a negative incline position, said negative incline position defining a second angle between said first longitudinal axis (B-B) and a negative inclined longitudinal axis (C"-C") which is negative with respect to the first longitudinal axis (B-B), said second angle being less than said predetermined initial inclination;
said distal tip portion comprising a plurality of notches formed in at least one side thereof, said plurality of notches facilitating articulation of said distal tip portion relative to said main body portion;
in said rest position distal tip extends straight along said second longitudinal axis (C-C), and in said positive incline position said distal tip extends straight along said positive inclined longitudinal axis (C'-C') at said first angle.

2. The endotracheal intubation device according to claim 1 wherein said distal tip portion is movable about a single axis when articulating between said resting position, said positive incline position, and said negative incline position.

3. The endotracheal intubation device according to claim 1 wherein said plurality of notches is uniformly spaced along said distal tip portion.

4. The endotracheal intubation device according to claim 1 wherein said plurality of notches comprises a first section of said plurality of notches defining a first spacing arrangement and a second section of said plurality of notches defining a second spacing arrangement, said first section being different than said second section.

5. The endotracheal intubation device according to claim 1 wherein said plurality of notches comprises a first section of said plurality of notches defining a first sizing arrangement and a second section of said plurality of notches defining a second sizing arrangement, said first section being different than said second section.

6. The endotracheal intubation device according to claim 1 wherein said plurality of notches are formed of filled with a first material elastic modulus and at least a portion of the remaining portion of said distal tip portion is made of a second material elastic modulus, said first material elastic modulus being different than said second material elastic modulus.

7. The endotracheal intubation device according to claim 1 wherein said deflection system includes a wire member.

8. The endotracheal intubation device according to claim 1 wherein said deflection system includes a single drive member disposed through a plurality of apertures formed in at least said distal tip portion, said plurality of apertures being offset from said second longitudinal axis.

9. The endotracheal intubation device according to claim 1 wherein said deflection system is retained within a bifurcated distal end of said distal tip portion.

10. The endotracheal intubation device according to claim 9 further comprising a cap member disposed on said bifurcated distal end of said distal tip portion.

11. The endotracheal intubation device according to claim 1 wherein said deflection system comprises:
a wire member, and
a slider member slidably disposed within a channel formed in said main body portion, said slider member being fixedly coupled with said wire member to exert a force upon said wire member in response to actuation by a user.

12. The endotracheal intubation device according to claim 11 wherein said slider member comprises a fore end engageable with a fore edge of said channel to limit movement of said slider member and positioning of said distal tip portion into said negative inclined position.

13. The endotracheal intubation device according to claim 11 wherein said slider member comprises an aft end engageable with an aft edge of said channel to limit movement of said slider member and positioning of said distal tip portion into said positive inclined position.

14. The endotracheal intubation device according to claim 1 wherein said predetermined initial inclination is about 15 degrees measured from said first longitudinal axis (B-B).

15. The endotracheal intubation device according to claim 1 wherein said first angle is in the range of about 30 to about 40 degrees measured from said first longitudinal axis (B-B).

16. The endotracheal intubation device according to claim 1 wherein said first angle is about 35 degrees measured from said first longitudinal axis (B-B).

17. The endotracheal intubation device according to claim 1 wherein said second angle is in the range of about minus 10 to about minus 20 degrees measured from said first longitudinal axis (B-B).

18. The endotracheal intubation device according to claim 1 wherein said second angle is about minus 15 degrees measured from said first longitudinal axis (B-B).

* * * * *